United States Patent

[19]

Massonne et al.

[11] Patent Number: 6,028,204

[45] Date of Patent: Feb. 22, 2000

[54] PROCESS FOR PREPARING PHTHALIDES

[75] Inventors: Klemens Massonne, Westheim; Rainer Becker, Bad Dürkheim; Wolfgang Reif, Frankenthal; Horst Neuhauser, Dudenhofen; Andreas Gieseler, Bad Dürkheim; Klaus Mundinger, Limburgerhof, all of Germany

[73] Assignee: BASF Aktiengesellschaft, Ludwigshafen, Germany

[21] Appl. No.: 09/202,478

[22] PCT Filed: Jun. 17, 1997

[86] PCT No.: PCT/EP97/03137

§ 371 Date: Dec. 16, 1998

§ 102(e) Date: Dec. 16, 1998

[87] PCT Pub. No.: WO98/01437

PCT Pub. Date: Jan. 15, 1998

[30] Foreign Application Priority Data

Jul. 3, 1996 [DE] Germany .......................... 196 26 659

[51] Int. Cl.⁷ ................................................ C07D 307/87
[52] U.S. Cl. ........................................... 549/307; 549/305
[58] Field of Search .................................... 549/305, 307

[56] References Cited

U.S. PATENT DOCUMENTS

| | | | |
|---|---|---|---|
| 2,079,325 | 5/1937 | Larchar | 260/123 |
| 2,114,696 | 4/1938 | Rolland | 260/123 |
| 4,528,385 | 7/1985 | aus der Funten | 549/307 |
| 5,296,614 | 3/1994 | Henkelmann et al. | 549/307 |

FOREIGN PATENT DOCUMENTS 28 03 319  8/1979  Germany .

OTHER PUBLICATIONS

J. Org. Chem. 51, 3439–3466, 1986.
Synthesis 223–224, 1985.

Primary Examiner—Amelia Owens
Attorney, Agent, or Firm—Keil & Weinkauf

[57] ABSTRACT

The disclosure is a process for preparing a phthalide of the general formula I

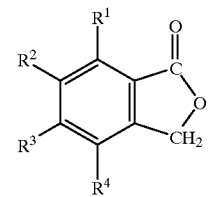

I where $R^1$, $R^2$, $R^3$ and $R^4$ are each independently of the others hydrogen, $C_1$–$C_4$-alkyl or $C_1$–$C_4$-alkoxy, by catalytic hydrogenation of a phthalic anhydride of the general formula II

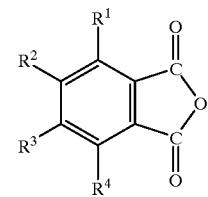

II where $R^1$, $R^2$, $R^3$ and $R^4$ are each as defined above, in a solvent, which comprises using said phthalide I, the reaction product of the catalytic hydrogenation, as solvent.

1 Claim, No Drawings

PROCESS FOR PREPARING PHTHALIDES

DESCRIPTION

The present invention relates to a process for preparing phthalides by catalytic hydrogenation of phthalic anhydrides in the phthalide as solvent.

DE-C-28 03 319 discloses a process for preparing phthalide by catalytic hydrogenation of phthalic anhydride in the gas phase, but this process is prohibitively costly at the product isolation stage, involving as it does multistage condensation and an attendant waste gas scrub.

It is further known to conduct the catalytic hydrogenation of phthalic anhydride to phthalide in inert solvents such as tetrahydrofuran (EP-A-0 542 037), benzoic esters optionally mixed with alcohols (EP-B-0 089 417), esters of lower monobasic alcohols with lower fatty acids (U.S. Pat. No. 2,079,325), lower monobasic aliphatic alcohols (U.S. Pat. No. 2,114,696).

Existing processes for the catalytic hydrogenation of phthalic anhydrides to phthalide in a solvent have the disadvantage of affording, as reaction products, mixtures of phthalide and solvent, which have to be separated by costly separating operations such as distillation and/or extraction to free the desired phthalides from the solvents used. In industry, where ecological and economic pressures dictate that the solvents be re-used, it is generally necessary to carry out additional process steps to recover the solvent(s).

It is an object of the present invention to remedy the aforementioned disadvantage of using solvents in the catalytic hydrogenation of phthalic anhydrides.

We have found that this object is achieved by a novel and improved process for preparing a phthalide of the general formula I

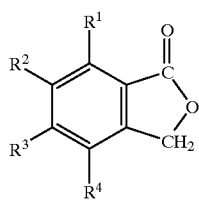

where $R^1$, $R^2$, $R^3$ and $R^4$ are each independently of the others hydrogen, $C_1$–$C_4$-alkyl or $C_1$–$C_4$-alkoxy, by catalytic hydrogenation of a phthalic anhydride of the general formula II

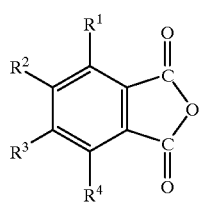

where $R^1$, $R^2$, $R^3$ and $R^4$ are each as defined above, in a solvent, which comprises using said phthalide I, the reaction product of the catalytic hydrogenation, as solvent.

It is surprising that the phthalide formed in the catalytic hydrogenation of phthalic anhydride can be used as solvent instead of an inert organic solvent, since it is known that phthalide can be further hydrogenated to form troublesome by-products such as o-tolylic acid and products which are hydrogenated in the aromatic nucleus and which are troublesome particularly in relation to the purification of the crude phthalide and which are very difficult to remove.

Compared with the use of the known organic solvents, the process of the invention has the advantage that the reaction mixtures obtained consist essentially of the phthalide product with small amounts of by-products. The phthalide can thus be isolated without a need for a solvent removal step and without additional cleaning steps for a solvent which is to be re-used. The novel process is thus distinguished from existing processes by simpler handling and by improved economy.

A further surprising advantage of the use of phthalide as solvent compared with the use of prior art solvents, for example compared with the use of butyrolactone as solvent, described in EP-A-0 542 037, is that the hydrogenation of phthalic anhydride to phthalide proceeds more rapidly. For instance, a comparison of the hydrogenation rates in butyrolactone and in phthalide as solvent shows that the hydrogenation rate in phthalide is about 3 times higher than that in butyrolactone.

The process of this invention can be carried out either by adding the phthalide solvent as such to the starting phthalic anhydride for the reaction, or by initially starting from phthalic anhydride and utilizing as reaction medium the phthalide formed in the course of the hydrogenation of the phthalic anhydride. If high melting phthalic anhydrides are used, it can be advantageous to use the phthalide as solvent from the start, since phthalide/phthalic anhydride mixtures have a lower melting point than the pure compounds. In addition, the heat of reaction is easier to remove from such mixtures from the start, owing to the dilution of the phthalic anhydride with the phthalide, so that this procedure is an advantage in batchwise operation in particular.

By contrast, in continuous operation, it can be advantageous to employ the alternative procedure of metering the phthalic anhydride into the reactor, it being diluted by the phthalide formed in the reactor.

The catalytic hydrogenation is generally carried out at temperatures from 50 to 400° C., preferably from 100 to 250° C., especially from 140 to 220° C., and at pressures from 1 to 400 bar, preferably from 5 to 300 bar, especially from 5 to 200 bar, particularly advantageously from 30 to 120 bar.

Customary hydrogenation reactors can be used, for example autoclaves or tubular reactors.

Examples of suitable hydrogenation catalysts are oxides or metals of the first to fourth main group of the Periodic Table of the Elements such as lithium, sodium, potassium, calcium, boron, aluminum, silicon and tin, of the first to eighth subgroup of the Periodic Table of the Elements such as titanium, zirconium, vanadium, niobium, chromium, molybdenum, manganese, rhenium, cobalt, nickel, ruthenium, rhodium, palladium, osmium, iridium, platinum, copper and silver and of the lanthanides group such as lanthanum, praseodymium, samarium, ytterbium or mixtures thereof.

Preference is given to using nickel catalysts, especially Raney nickel. The hydrogenation catalysts can be used for example in the form of supported catalysts, homogeneous catalysts or suspended catalysts.

The weight ratio of phthalic anhydride to be hydrogenated to the phthalide used as solvent is generally within the range from 1000:1 to 1:1000, preferably within the range from 500:1 to 1:500, especially within the range from 200:1 to 1:200. These ranges apply to the continuous process after the steady-state operating conditions governing continuous operation have become established after the start-up.

In a preferred embodiment of the process of this invention, the reaction of the invention is discontinued as soon as all the phthalic anhydride used has been hydrogenated. The time for discontinuation is determined for example by determining the phthalic anhydride still present, for example by gas chromatography or from the time course of hydrogen consumption. This procedure affords selectivities of more than 80% in respect of the phthalide formed.

The reaction product is worked up in a conventional manner, preferably by distillation.

In the compounds I and II, $R^1$, $R^2$, $R^3$ and $R^4$ are each independently of the others hydrogen; $C_1$–$C_4$-alkyl such as methyl, ethyl, n-propyl, isopropyl, n-butyl, isobutyl, sec-butyl, tert-butyl, preferably methyl and ethyl, especially methyl; $C_1$–$C_4$-alkoxy such as methoxy, ethoxy, n-propoxy, isopropoxy, n-butoxy, isobutoxy, sec-butoxy, tert-butoxy, preferably methoxy and ethoxy, especially methoxy. $R^1$, $R^2$, $R^3$ and $R^4$ are particularly preferably all hydrogen.

The phthalic anhydrides II used as starting materials are well known, such as phthalic anhydride itself, or can be obtained by known processes (J. of Org. Chemistry 51, 3439–3446 (1986); Synthesis 223–224 (1985)).

The phthalides I are used for example as starting materials for the synthesis of crop protection agents.

The Examples which follow illustrate the invention.

INVENTIVE EXAMPLE 1

A 2 l autoclave equipped with a lift stirrer is charged with 413 g of phthalic anhydride, 964 g of phthalide (688.5 g of phthalic anhydride and 688.5 g of phthalide for run 1d) and the amount of the Raney nickel hydrogenation catalyst indicated in the table, as a melt. After inertization with nitrogen and replacement for hydrogen, the contents are heated to the stated temperature at a lift number of 160 per minute and the hydrogen is pressed in to the stated pressure. The hydrogenation is continued under these conditions to a phthalic anhydride conversion of more than 99% (monitored by gas chromatography).

The experimental conditions and results are summarized in the following table:

| Run No. | Temperature °C. | Pressure bar | Catalyst quantity g | Hydrogen consumption l(S.T.P.) | Hydrogenation time min | Conversion % | Selectivity % |
| --- | --- | --- | --- | --- | --- | --- | --- |
| 1a | 170 | 40 | 4.13 | 136 | 365 | 100 | 75 |
| 1b | 183 | 80 | 1.03 | 137 | 1162 | 100 | 80 |
| 1c | 183 | 80 | 1.45 | 137 | 435 | 100 | 85 |
| 1d | 183 | 80 | 5.16 | 208 | 164 | 99 | 87 |
| 1e | 180 | 80 | 42.4 | 120 | 80 | 100 | 80.5 |

INVENTIVE EXAMPLE 2

A 0.5 l stirred autoclave equipped with a sparging stirrer is charged with 88.8 g of phthalic anhydride, 207.2 g of phthalide and 0.90 g of Raney nickel (B 113 N from Degussa) as a melt at about 120° C. After the stirrer has been switched on, hydrogen is pressed in to a pressure of 40 bar, and the temperature is raised to 180° C. Hydrogenation is continued at this pressure and at this temperature to a phthalic anhydride conversion greater than 99% using a stirrer speed of 500 (run 2a) or 1000 (run 2b) revolutions per minute (rpm).

| Run No. | Speed rpm | Hydrogenation time min | Conversion % | Selectivity % | Hydrogen consumption l (S.T.P.) |
| --- | --- | --- | --- | --- | --- |
| 2a | 500 | 235 | 99.9 | 85 | 25.1 |
| 2b | 1000 | 225 | 99.7 | 83 | 24.8 |

| | Composition of products in % by weight | | | |
| --- | --- | --- | --- | --- |
| Run No. | Phthalide | Water | Phthalic anhydride | o-Tolylic acid |
| 2a | 92.3 | 3.3 | <0.1 | 3.2 |
| 2b | 91.9 | 3.4 | 0.1 | 3.7 |

INVENTIVE EXAMPLE 3

A 2 l autoclave equipped with a lift stirrer is charged with 592 g of phthalic anhydride, 785 g of phthalide and 35 g of Raney nickel in the form of a melt. After inertization with nitrogen and replacement with hydrogen, the contents are heated to the stated temperature at a lift number of 160 per minute and hydrogen is pressed in to a pressure of 80 bar. Hydrogenation is continued under these conditions to a phthalic anhydride conversion of greater than 99% (monitored by gas chromatography).

The experimental conditions and results are summarized in the following table:

| Run No. | Temperature °C. | Hydrogen consumption l (S.T.P.) | Hydrogenation time min | Conversion % | Selectivity % |
| --- | --- | --- | --- | --- | --- |
| 3a | 140 | 172 | 200 | 99 | 82 |
| 3b | 160 | 170 | 160 | 99.5 | 83 |

INVENTIVE EXAMPLE 4

The apparatus described in Inventive Example 3 is charged with a solution of 43% by weight of phthalic anhydride in phthalide and water-moist Raney nickel in an amount of 5.9% by weight, based on phthalic anhydride, and used to carry out a hydrogenation in the manner of Inventive Example 3 at a pressure of 80 bar and a temperature of 140° C. until 75% of the theoretically required amount of hydrogen is consumed. The time to this hydrogen consumption is determined.

| Run No. | Time to 75% hydrogen consumption min |
|---|---|
| 4a | 117 |
| 4b | 105 |
| 4c | 108 |

COMPARATIVE EXAMPLE

The runs of Inventive Example 4 are repeated using butyrolactone as solvent instead of phthalide. The following hydrogenation time was found:

| Run No. | Time to 75% hydrogen consumption min |
|---|---|
| 5a | 285 |
| 5b | 390 |
| 5c | 357 |
| 5d | 380 |

When butyrolactone is used as solvent for the phthalic anhydride hydrogenation the reaction time required is from 2.4 to 3.5 longer than that required using phthalide as solvent (Inventive Example 4) to obtain a comparable conversion.

We claim:
1. A process for preparing a phthalide of the general formula I

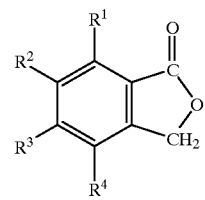

where $R^1$, $R^2$, $R^3$ and $R^4$ are each independently of the others hydrogen, $C_1$–$C_4$-alkyl or $C_1$–$C_4$-alkoxy, by catalytic hydrogenation of a phthalic anhydride of the general formula II

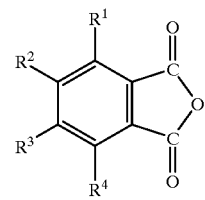

where $R^1$, $R^2$, $R^3$ and $R^4$ are each as defined above, in a solvent, which comprises using said phthalide I, the reaction product of the catalytic hydrogenation, as solvent.

* * * * *